United States Patent
Holzer et al.

(10) Patent No.: US 8,340,740 B2
(45) Date of Patent: Dec. 25, 2012

(54) GARMENT FOR MONITORING PHYSIOLOGICAL PROPERTIES

(75) Inventors: Christian Holzer, Munich (DE); Thorsten Habel, Walzbachtel (DE); Martin Gierich, Stutensee (DE)

(73) Assignee: Cairos Technologies AG, Karlsbad (DE)

( * ) Notice: Subject to any disclaimer, the term of this patent is extended or adjusted under 35 U.S.C. 154(b) by 546 days.

(21) Appl. No.: 12/579,284

(22) Filed: Oct. 14, 2009

(65) Prior Publication Data

US 2010/0198043 A1    Aug. 5, 2010

(30) Foreign Application Priority Data

Oct. 14, 2008 (DE) .......... 10 2008 051 536

(51) Int. Cl.
*A61B 5/0408* (2006.01)
(52) U.S. Cl. ......... 600/388; 600/382; 600/389; 600/509
(58) Field of Classification Search .......... 600/382, 600/388, 389, 509; 439/909
See application file for complete search history.

(56) References Cited

U.S. PATENT DOCUMENTS

| | | | |
|---|---|---|---|
| 6,941,775 B2 | 9/2005 | Sharma | |
| 7,319,895 B2 * | 1/2008 | Klefstad-Sillonville et al. | 600/388 |
| 2004/0138546 A1 * | 7/2004 | Reho et al. | 600/382 |
| 2005/0010096 A1 | 1/2005 | Blackadar | |
| 2006/0041200 A1 * | 2/2006 | Dotter et al. | 600/502 |
| 2006/0111640 A1 * | 5/2006 | Shen et al. | 600/509 |
| 2006/0211934 A1 * | 9/2006 | Hassonjee et al. | 600/372 |
| 2007/0078324 A1 * | 4/2007 | Wijisiriwardana | 600/386 |
| 2007/0089800 A1 * | 4/2007 | Sharma | 139/388 |
| 2008/0058658 A1 * | 3/2008 | Noguchi | 600/508 |
| 2009/0265828 A1 * | 10/2009 | Semba et al. | 2/69 |
| 2009/0270708 A1 * | 10/2009 | Shen et al. | 600/389 |
| 2010/0185076 A1 * | 7/2010 | Jeong et al. | 600/388 |

FOREIGN PATENT DOCUMENTS

| | | |
|---|---|---|
| EP | 1731090 | 12/2006 |
| WO | WO 01/01855 | 1/2001 |
| WO | WO 02/30279 | 4/2002 |
| WO | WO 2005/013816 | 2/2005 |
| WO | WO 2007/040878 | 4/2007 |
| WO | WO 2007/050650 A2 | 5/2007 |

\* cited by examiner

*Primary Examiner* — Lee S Cohen
*Assistant Examiner* — Erin M Cardinal
(74) *Attorney, Agent, or Firm* — Michael A. Glenn; Glenn Patent Group (57) ABSTRACT

A garment enables the monitoring of physiological properties of a person wearing the garment. The measuring sensors are integrated into the garment and are positioned by wearing the garment to the correct position of the body of the person wearing the garment. The device for monitoring the physiological properties containing the measuring electronics is located in the back portion of the garment. This device is either fixedly integrated into the garment or it can be removed.

11 Claims, 4 Drawing Sheets back view

GARMENT FOR MONITORING PHYSIOLOGICAL PROPERTIES

BACKGROUND OF THE INVENTION

1. Field of the Invention

The present invention generally refers to the measurement of physiological properties of a person, particularly of the heart rate when playing team sports or ball games.

2. Description of the Prior Art

The measurement of the heart rate during training is of decisive meaning for an optimum and healthy fitness and endurance training. While the manual sensing of the heart beat supplies imprecise results, conventional electrocardiogram (ECG) devices are too cost-intensive and too complex during sport.

The first wireless heart rate measuring device (also known as pulse monitor watch or pulse meter) was the portable PE 2000 of Polar Electro OY. The PE 2000 heart rate measuring device is composed of a receiver and a transmitter that is either attached by disposable electrodes or an elastic electrode belt on the chest. The receiver is a watch-like monitor that can be worn around the wrist.

The conventional heart rate measuring devices record the heart signals (R-pulses) via a transmitter worn on the chest, said pulses being output via the skin, and transmit these signals to the receiver that is worn around the wrist or that is attached on a bicycle or piece of sports equipment. The current heart rate is then continuously shown on the display of the receiver.

In the fitness sector, stationary heart rate meters are often used on the devices themselves that collect the heart rate via sensors that must be comprised for the measurement. Other devices measure the heart rate on the earlap. However, the two last mentioned measuring methods are not suitable for the competitive sports sector.

WO 07/040,878 A1 discloses a further development of the conventional heart rate measuring devices. In this publication, the electrodes are integrated into a garment to measure the heart beat. Two electrodes are located on the front side of the garment and one electrode is located on the rear side. Furthermore, a device for processing the signals measured is either integrated in the garment or can be attached on the garment for instance mechanically by means of pushbuttons.

A similar device is offered by Adidas in collaboration with Polar Electro. In this case a heart rate meter can directly be attached on the chest on a T-shirt. This system also makes a chest belt superfluous.

However, these conventional systems for measuring the heart rate are suitable to only a limited extent for persons practicing a team or ball sport. Particularly in the case of ball sport the chest portion or the entire front portion of the upper part of the body is often integrated in the game. Soccer players for instance stop a cross by the chest. The same is true for basketball players, in which the front portion of the upper part of the body often contacts the ball when stopping or passing the ball. According to this, sensors in the chest area are felt uncomfortable in such cases. Above that, sensors in the chest area are at risk of being hit by a ball. If the processing and/or transmission unit is also located in the chest area, as in the Adidas-system, the risk of injury of the player is also increased. The risk of injury is also increased by the pressure connections for being coupled to the processing unit suggested in WO 07/040,878 A1.

SURVEY OVER THE INVENTION

A garment is provided which enables monitoring of physiological properties of persons practicing a team or ball sport. In an embodiment, the garment comprises a device for monitoring physiological properties of person wearing the garment. This monitoring device is positioned on the rear side of the garment. The monitoring device can also be adapted to receive and further process physical signals characterizing the physiological properties of the person wearing the garment to be monitored. Furthermore, the monitoring device can be adapted to store and transmit measuring results resulting from the further processing of the physical signals.

In some embodiments, the garment can also have two conductive electrodes and conductive connections from the conductive electrodes to the monitoring device. The monitoring device can be detachably connected to the garment. Furthermore, the monitoring device can comprise conductive contacts at a surface and the garment can comprise conductive contacts at a surface of the rear side, wherein the conductive contacts of the monitoring means can be detachably connected to the conductive contacts of the garment. Furthermore, the garment can comprise a conductive connection from the conductive electrodes to the conductive contacts on the surface of the garment. In some embodiments, the conductive electrodes can be composed of a conductive stretch fabric. The conductive connections from the conductive electrodes to the conductive contacts can be made of conductive thread, and the conductive contacts on the surface of the rear side of the garment and the conductive contacts on the surface of the monitoring device can be conductive Velcro® fasteners.

The garment can also comprise non-conductive fibers and the conductive connections from the conductive electrodes to the conductive contacts on the surface of the garment can be woven into the non-conductive fibers of the garment. In other embodiments, at least part of the garment is made of non-conductive fibers, and the conductive connections of conductive electrodes to the conductive contacts can be glued or stitched onto the surface of the garment onto the part of the garment made of the non-conductive fibers.

In some embodiments, the conductive electrodes form an inner surface of the garment, and the two electrodes are located symmetrical with respect to the spine of the person wearing it when the garment is worn. The two electrodes can extend laterally between the fleeing ribs and the costal arch of the wearer starting from the front side of the garment in the direction of the rear side of the garment up to between the scapulae of the wearer when the garment is worn.

The monitoring device can also comprise a processor, a memory, an USB interface, a firewall interface, a wi-fi module, a Bluetooth interface, a GSM module, a GPRS module, an UMTS module or a GPS module.

In some embodiments, the physiological property to be monitored can be the heart rate and the monitoring device can be adapted to measure electrical potentials at the electrodes.

In some embodiments, the conductive contacts of the garment can be attached to an outer surface on the rear side of the garment, and the conductive contacts of the garment can in the worn state be located either right or left of the spine of the wearer. Furthermore, the conductive contacts of the garment can in worn state be located in the shoulder area of the wearer, and the conductive connections from the conductive electrodes to the conductive contacts can have an identical electrical resistance. In some embodiments, the conductive contacts of the garment can be arranged in the worn state in the loin region of the wearer, and the conductive connections from the conductive electrodes to the conductive contacts can have an identical electrical resistance. Furthermore, the conductive contacts can be attached on an outer surface on the rear side of the garment and the conductive contacts of the garment can in the worn state be located symmetrical right and left of the spine of the wearer. Finally, the conductive contacts can be attached at an inner surface on the rear side of the garment, and the conductive contacts of the garment can be located in the worn state on the neck area of the wearer.

SHORT DESCRIPTION OF THE DRAWINGS

The attached drawings are inserted into the description and form part of same for the purpose of explaining the principles of the invention. The drawings shall not be understood in that they restrict the invention to only the examples shown and described as the invention can be practiced and applied. Further features and advantages can be derived from the following detailed description of the invention and are also shown in the attached drawings, the drawings showing in detail.

DETAILED DESCRIPTION OF THE INVENTION

For optimal training success, the training must be adapted to the physiology of the athlete. For this purpose, a monitoring of physiological properties of the sports exercising person during training is indispensable. Important physiological properties that lead to optimization of the training but which are also important for medical purposes can be the heart rate, the breathing rate, the oxygen saturation of the blood, the blood circulation of the individual organs, the identification of the muscular groups used or the stress on the skeletal structure.

A plurality of measuring methods and sensors are conceivable to monitor the physiological properties. The record of an electrocardiogram (ECG) for instance provides conclusive findings on the activity of the heart during training. If only the heart rate is of interest, a complete ECG does not have to be made, but only the R-pulse of the heart must be evaluated.

To monitor the physiology of individual organs during the training, it is also conceivable to make sonograms with or without the application of a Doppler process. By the aid of a Doppler ultrasound sonography, statements can for instance be made on the blood flow in the heart during exercising the sport. Furthermore, ultrasound measurements during the training can provide information about the stress on the skeletal structure.

Besides that, the use of other sensors, such as infrared sensors for detecting specific active regions in the body or motion sensors for optimizing movement cycles are possible. The use of radioactive tracer substances is also conceivable to measure the flow rate of the blood. In this case, the propagation of a radioactive tracer substance injected into the blood circulation of the athlete is determined by means of measurement of the radioactive activity.

The sensors, the measuring electronics and other processing units for monitoring the physiological properties of athletes during the training must not or only marginally disrupt the normal work movement of the athlete in order to be accepted by the athletes and trainers. Furthermore, the measurement of physiological properties with a disrupted work movement would not optimize normal training but the disrupted training.

Mostly in team or ball sports, special demands on the performing devices have to be met in terms of the monitoring of physiological properties when exercising the sport. It is not unusual that the chest portion of the athlete, particularly in ball sports, frequently contacts a game item or another player. The risk exists that the sensors for monitoring the physiological properties, e.g. upon impingement of a ball, are damaged. Furthermore, most of the ball or team sport athletes feel technical equipment in the front area of the upper part of the body as uncomfortable. Finally, the risk of injury is increased by attaching measuring instruments on the front side of the upper part of the body.

According to an embodiment of the invention, the complete measuring equipment required for monitoring the physiological properties of an athlete is integrated into a garment. Furthermore, the correct placing of the measuring device is implemented by correctly wearing the garment. The garment preferably covers the upper part of the body of the person to be monitored. The garment may be a pullover, a T-shirt, an undershirt or any other garment that the athlete wears when exercising his/her sport. For the measurement of some physiological properties it may, however, be advantageous, to integrate the measuring device and/or sensors into a different garment, for instance a pair of trousers or a helmet. The fact that the athlete must wear only one garment to monitor physiological events or properties increases the acceptance of the athlete, since complicated attachment of the measuring system is not required.

In many cases it is required to distinguish between measuring sensors and measuring electronics. The measuring electronics processes physical signals recorded by the measuring sensors and which characterize physiological properties. The measuring results, such as the heart rate or breathing frequency, result from this processing. Both, measuring sensors and well as measuring electronics can often be accommodated in a commonly used device, which is then integrated at a certain location in the garment. In other embodiments it is, however, sensible, to spatially separate the measuring electrode from the sensors. The sensors can in this case be positioned at the locations in the garment required for measurement, whereas the measuring electronics, which is usually bulkier than the sensors, is integrated into the garment at another location.

Embodiments of the invention also enable the transmission of the measuring results of physiological properties during exercise of the sport. For this purpose, a transmission unit is integrated into the garment in addition to the measuring electronic and in addition to the measuring sensors. In some embodiments of the invention, the transmission unit uses a device together with the measuring sensors and the measuring electronic and is therefore positioned at the same location in the garment. However, the transmission of signals often affects measurements of physiological properties. According thereto, the transmission unit is spatially separated from the measuring sensors in other embodiments and can for instance use a common device together with the measuring electronics. In still a different alternative embodiment, the transmission unit is spatially separated both from the measuring sensors as well from the measuring electronics in the garment. In these cases, the measuring electronics communicates with the transmission unit either via a cable connection or it communicates wireless by means of a close-up range communication method, such as Bluetooth.

However, in all embodiments, the chest portion of the garment is kept free from measuring electronics and transmission unit. Furthermore, the measuring sensors are, if possible, also positioned such that the chest area of the garment is kept free.

Figure 1A:
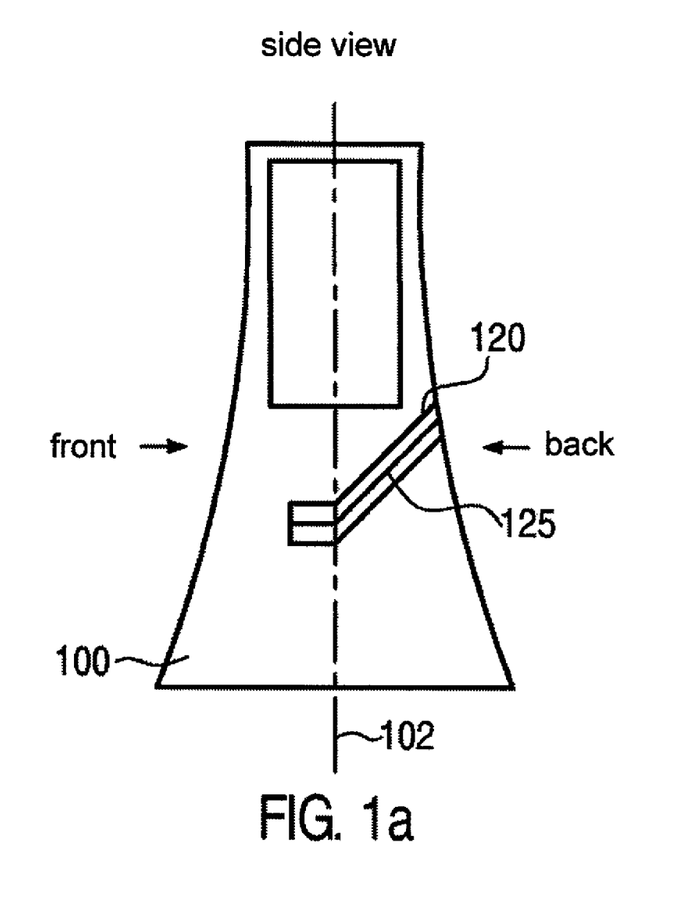
FIG. 1a shows a side view of the garment for monitoring physiological properties according to an embodiment.
Figure 1B:
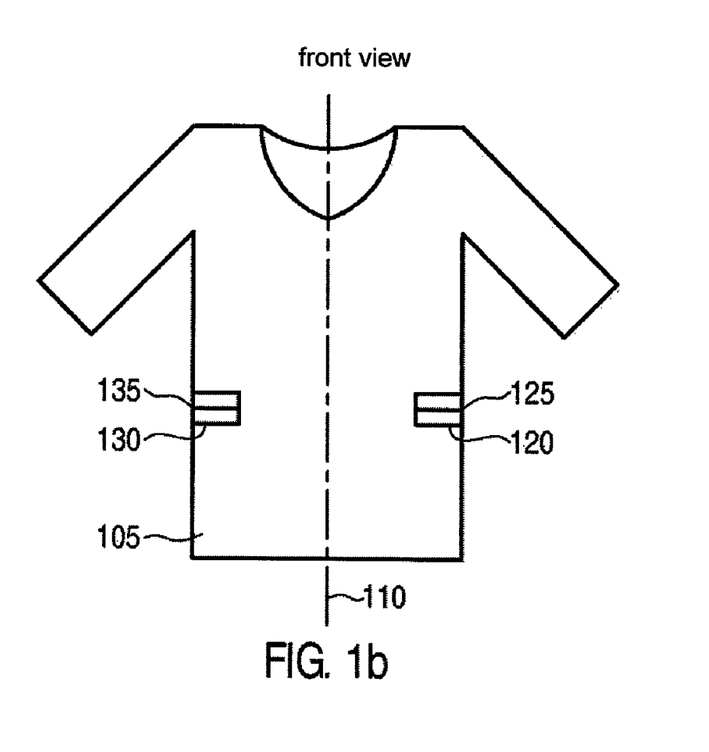
FIG. 1b shows a front view of the garment for monitoring physiological properties according to an embodiment.
Figure 1C:
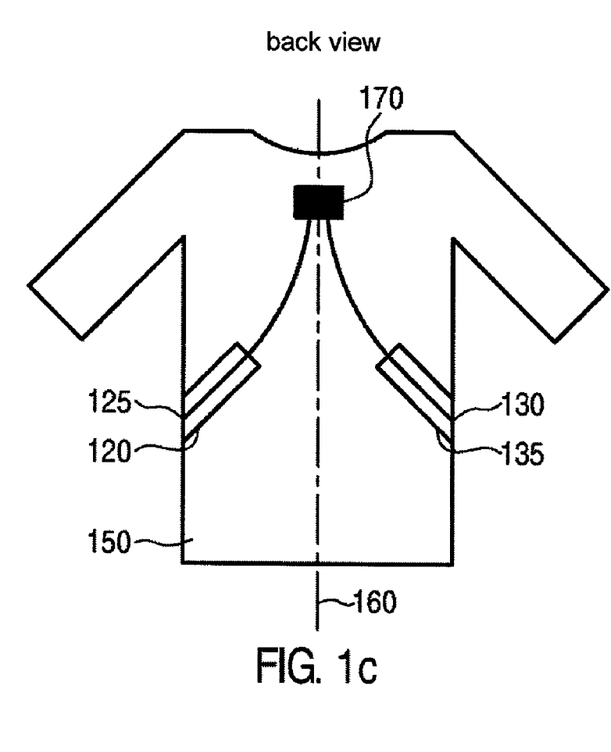
FIG. 1c shows a back view of the garment for monitoring physiological properties according to an embodiment.

FIGS. 1a to 1c show an exemplary garment 100 for monitoring physiological properties. Principles of the present invention shall be explained exemplarily by means of measuring the heart rate. However, as mentioned above, other physiological properties can also be monitored and evaluated by means of suitable sensors and measuring electronic.

According to an embodiment in FIG. 1a, the device for monitoring physiological properties is integrated into a T-shirt worn by the athlete during exercising the sport. Of course, the device for monitoring physiological properties can, as stated above, also be integrated into other garments, such as pullovers or tank tops.

FIG. 1a shows a garment 100 for measuring the heart rate of the wearer in a side view. The auxiliary line 102 divides the garment 100 into the front side and the rear side. According to an embodiment of the present invention, the electrodes contacting the skin of the wearer form the measuring sensors for monitoring the heart rate. In FIG. 1a, an electrode 120 is exemplarily shown that is integrated into the garment in a manner that it extends in the worn state laterally on the rips of the wearer starting in the direction of the wearer towards the scapulae. The electrode is positioned in an embodiment in a manner that as few bones as possible are located below the electrode 120 in the worn state.

In order to further specify the position of the electrodes, line 110 in FIG. 1b and line 160 in FIG. 1c define the position of the spine in the worn state of the garment 100. The length of the line 110 and the length of the line 160, respectively, does not correspond to the length of the spine. The lines 110 and 160 are, exactly as line 102 of FIG. 1a, only meant as auxiliary lines for better understanding the invention.

As may be seen from FIGS. 1a to 1c, the electrode 120 is positioned such that it extends laterally between the fleeing ribs and the costal arch of the wearer starting at the front side 105 of the garment 100 in the direction of the rear side 150 of the garment 100 up to between the scapulae of the wearer. Particularly, the electrode 120 can first of all extend horizontally on the front side 105 of the garment 100, to then rise on the rear side 150 of the garment 100 linearly in the direction towards the upper thoracic spine. Of course, the electrode 120 can also be formed in a different manner. A shape is particularly suitable that follows a space between the ribs of the thorax of the wearer. This leads to a curved shape on the rear side 150 of the garment 100.

As may be seen from FIG. 1b, which shows the front side of the garment 100, and FIG. 1c, which shows the rear side of the garment 100, a further electrode 130 is integrated in the garment 100 symmetrical to the spine of the wearer, said further electrode basically having the same properties as the electrode 120. In an embodiment, the electrode can, however, also be guided along a different space between the ribs of the wearer than the electrode 120. In these embodiments, the electrode 130 is therefore offset vertically with respect to the electrode 120.

The electrodes 120 and 130 form an inner surface of the garment 100. In an embodiment they are formed of a conductive stretch material. The stretch material can be a lycra-like material. It can for instance be composed of approx. 92% silver-coated nylon and approx. 8% dorlastan. The surface resistance of such a material in unstretched condition less than 1 $\Omega$/sq. The Thickness is approx. 0.5 mm with a weight of approx. 130 g/m$^2$.

In some embodiments, the electrodes 120 and 130 are stitched or glued onto the inner surface of the garment 100. The parts of the garment 100 onto which the electrodes 120 and 130 are stitched or glued on can be composed of non-conductive fibers to insulate the electrodes towards the outside. However, the electrodes 120 and 130 can also be sewed into the garment 100 itself or they can be integrated in a different manner.

As may further be seen from FIG. 1b to 1c, each electrode 120 and 130 contacts a conductive connection 125 and 135, respectively. The conductive connections 125 and 135 are either adhered or stitched onto the electrode 120 or 130 in the longitudinal direction. In some embodiments, the conductive connections are woven into the stretch material that forms the electrodes.

Figures 3A, 3B, 4:
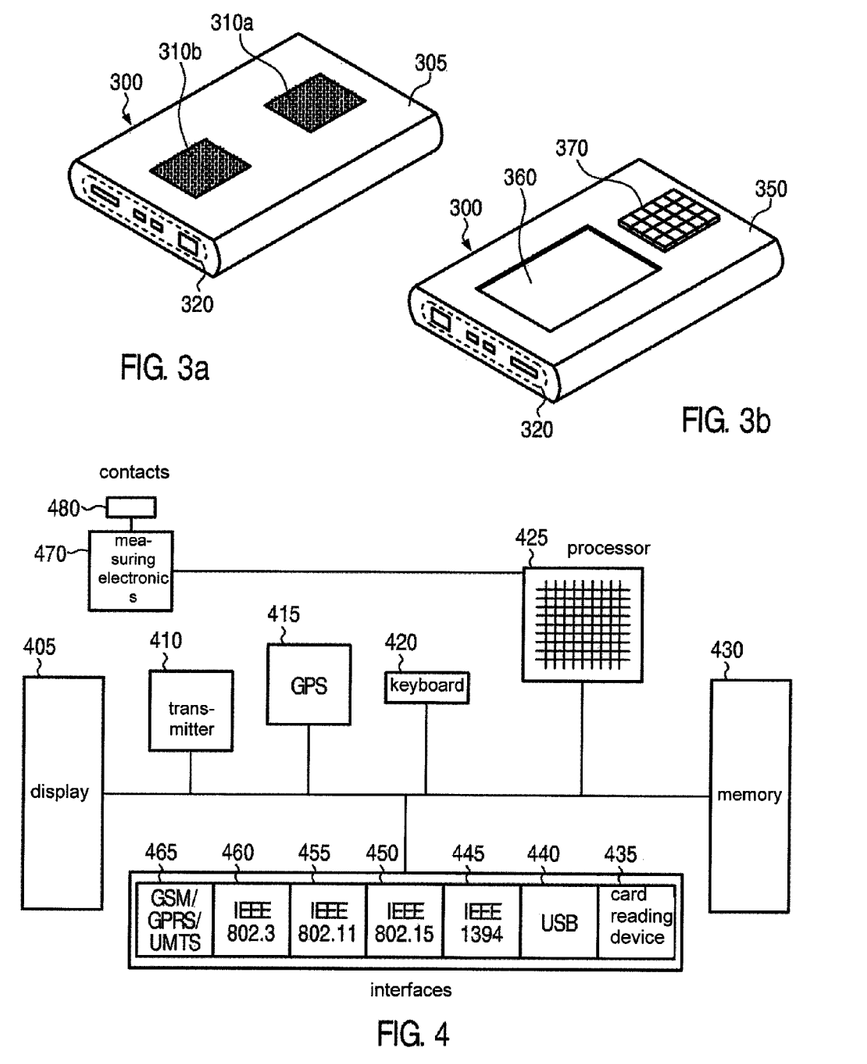
FIG. 3a shows a perspective view of a device for monitoring physiological properties according to an embodiment.
FIG. 3b shows a perspective view of a device for monitoring physiological properties according to an embodiment.
FIG. 4 shows a schematic view of a device for monitoring physiological properties according to an embodiment.

The conductive connections 125 and 135, respectively, lead from the electrodes 120 or 130 to a device 170 for monitoring physiological properties, which is specified with respect to FIG. 3a and FIG. 3b as well as FIG. 4.

The conductive connections 125 and 135 can be composed of a conductive yarn or thread that is woven into the non-conductive fibers of the garment 100 or that is sewed/stitched or adhered onto the garment 100. Such a thread is for instance composed of silver-coated nylon whose resistance is less than 5 $\Omega$/cm.

The conductive connections are electrically conductively coupled to the device for monitoring the physiological properties. As described above, and as explained further below with reference to FIGS. 3a and 3b as well as FIG. 4, the device 170 contains a measuring electronics in some embodiments that is required for a heart rate measurement. In some embodiments, the device 170 is fixedly integrated into the garment 100, in other embodiments it is detachable from the garment 100, as explained in detail with reference to FIGS. 2a to 2c. The device 170 is preferably positioned on the rear side 150 of the garment 100.

In some embodiments, the device 170 also comprises a transmission unit that transmits the results of the measurement of physiological properties by means of a wireless transmission method to an external receiver. In other embodiments, the transmission unit is, as mentioned above, spatially separated from the device 170 that contains the measuring electronic. The measuring electronic can for instance fixedly be integrated into the garment 100 while the transmission unit is detachable or vice versa.

In the case of the heart rate measurement, the measuring electronic in the device 170 detects electrical potentials at the electrodes 120 and 130. Since each contraction of the myocardial is preceded by en electrical excitement, conclusions can be drawn on the heart in general and the heart rate in particular by deriving electrical potentials on the surface of the body. In order to minimize the influence of the lines 125 and 135 to the electrodes 120 and 130, the conductive connections in some embodiments have an identical electrical resistance.

Of course, in some embodiments of the invention, more than two electrodes can be used for measuring the heart rate. In this case, individual electrodes can either be short-circuited, e.g. by means of conductive connections, or each individual electrode can have its own conductive connection to the device 170.

Figures 2A, 2B, 2C:
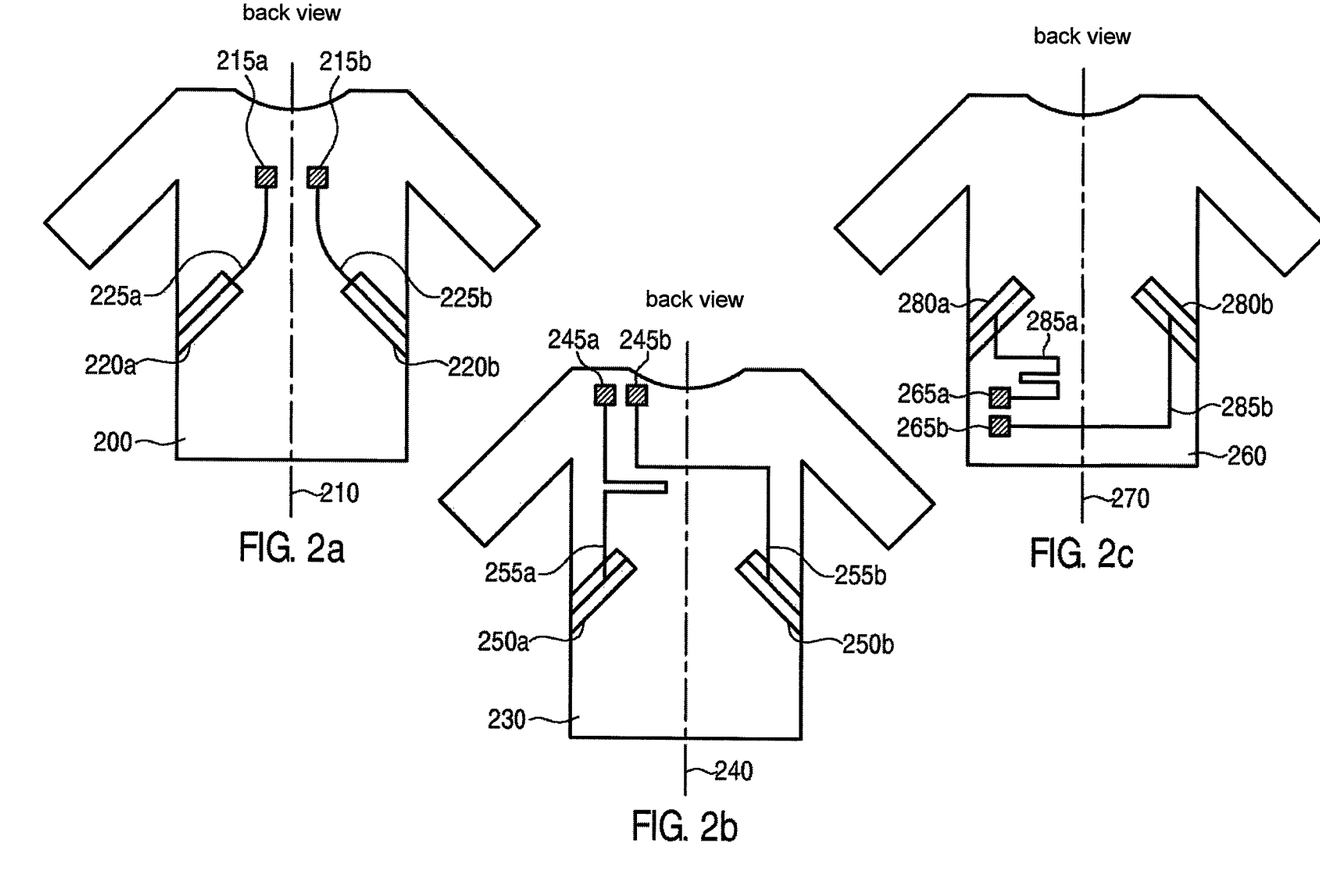
FIG. 2a shows a back view of the garment for monitoring physiological properties according to an embodiment.
FIG. 2b shows a back view of the garment for monitoring physiological properties according to an embodiment.
FIG. 2c shows a back view of the garment for monitoring physiological properties according to an embodiment.

FIGS. 2a to 2c show embodiments of the invention, in which the device 170 for monitoring physiological properties can be removed from the rear side 200, 230 or 260 of the garment 100. Similar to the auxiliary line 160 of FIG. 1c, the auxiliary line 210 in FIG. 2a, the auxiliary line 240 in FIG. 2b as well as the auxiliary line 270 in FIG. 2c define the position of the spine in the worn state of the garment.

In these embodiments, the conductive connections 225a and 225b of FIG. 2a, 255a and 255b of FIGS. 2b and 285a and 285b of FIG. 2c each end in the conductive contacts 215a and 215b of FIG. 2a, 245a and 245b of FIG. 2b as well as 265a and 265b of FIG. 2c. The conductive contacts 215a/b, 245a/b, as well as 265a/b form a surface of the garment 100. Of course, the number of the contacts is not limited to two. In embodiments, in which more than two electrodes are used for measuring the heart rate, each electrode can conductively be connected to a respective contact.

The electrodes 220a and 220b of FIG. 2a, electrodes 250a and 250b of FIG. 2b as well as electrodes 280a and 280b of FIG. 2c correspond to electrodes 120 and 130 of FIGS. 1a to 1c. The same applies to the conductive connections 225a and 225b of FIG. 2a, connections 255a and 255b of FIG. 2b as well as connections 285a and 285b of FIG. 2c, which are formed similarly as the connections 125 and 135 of FIGS. 1a to 1c.

The conductive contacts 215a and 215b of FIGS. 2a, 245a and 245b of FIG. 2b as well as 265a and 265b of FIG. 2c a can be hook/loop bands of a conductive Velcro® fastener. In such embodiments, the device 170 for monitoring physiological properties has the respective counterpieces of the hook/loop belts on a surface, as specified in FIG. 3a. The Velcro® fasteners then connect the electrodes for discharging the electrical potentials to the surface of the skin with the measuring electronic in the device 170 for measuring the heart rate. The resistance of the hook band is approx. 1.8 Ω/sq and the resistance of the loop band is for instance 1.4 Ω/sq. The expected life of such a Velcro® fastener is approx. 5000 opening procedures.

As described above, only the transmission/memory means for the measuring results of the device 170 can detachably be connected to the contacts on the surface in an alternative embodiment, whereas the device 170 with the measuring electronics is fixedly integrated into the garment. In such cases, the conductive connections, e.g. made of a conductive thread as described above, lead from the measuring electronics to the conductive contacts to couple the transmission/memory unit with the device 170.

FIG. 2a shows a garment, in which the device 170 for monitoring physiological properties is removed. The two contacts 215a and 215b are electrically coupled to the electrodes 220a and 220b by means of the conductive connections 225a and 225b. In this embodiment, the contacts 215a and 215b are positioned on an outer surface of the rear side 200 of the garment in a manner that if the garment is worn, they are located symmetrically left and right of the spine of the wearer. The supply lines 225a and 225b are in some embodiments adapted such that they have an identical resistance.

In an alternative embodiment, as illustrated in FIG. 2b, the contacts 245a and 245b are positioned on an outer surface of the rear side 230 of the garment such than if the garment is worn, they are located in the shoulder area of the wearer. The contacts 245a and 245b can be integrated into the left or right shoulder area of the garment. An advantage of this embodiment compared to the embodiment of FIG. 2a is that the removable device 170 when wearing the garment can easily be attached and removed by the wearer himself. Furthermore, the device 170 does not rest on the spine of the wearer, which further minimizes the risk of injury.

As can be seen in FIG. 2b, the electrical resistances of the conductive connections 255a and 255b in this embodiment are adapted to one another in that the length of the connections 255a corresponds to the length of the connection 255b. This is realized in some embodiments in that the length of the conductive connection 255a from the electrode 25a, which is located closer to the contacts 245a and 245b, is extended by inserting loops, i.e. the electrode 250a is not connected by the shortest way with the contact 245a.

A further alternative embodiment is shown in FIG. 2c. In this case, the conductive contacts 265a and 265b are positioned on an outer surface of the rear side 260 of the garment in a manner that if the garment is worn, they are located in the lateral loin portion of the wearer. Similar to the embodiments of FIG. 2b, the contacts 265a and 265b can be located either left or right of the spine of the wearer. In this case, the conductive connection 285a from the electrode 280a, which is located closer to the contacts 265a and 265b is not guided directly to the electrical contact, but it is extended such that the resistance of the conductive connection 285a corresponds to the one of the conductive connection 285b.

Of course, the contacts 245a and 245b of FIG. 2b can also be arranged in a manner differently than shown. Instead of being arranged horizontally, they can also be arranged vertically or diagonally with respect to each other. The same applies to contacts 265a and 265b of FIG. 2c. The contacts 215a and 215b of FIG. 2a can also be arranged vertically and can be positioned either left or right of the spine of the wearer. In some embodiments, the contacts 215a and 215b are also located precisely on the spine of the wearer. Furthermore, the contacts 245a and 245b can also be positioned on a sleeve, in case a sleeve exists, on the rear side 230 of the garment.

In alternative embodiments the electrical contacts 215a, 215b, 245a, 245b, 265a and 265b are not positioned on an outer surface on the rear side of the garment but on an inner surface of the rear side of the garment. This has the advantage that the device 170 for monitoring physiological properties cannot incidentally be stripped off when exercising the sport, e.g. when contacting another player or when contacting a play item. In a preferred embodiment the contacts are positioned in the neck area of the wearer.

FIGS. 3a and 3b show perspective views of a device 300 for monitoring physiological properties. In some embodiments, the device 170 for monitoring physiological properties corresponds to the device 300. The device 300 substantially contains a measuring electronics, which further processes measured physical signals and therefore supplies measuring results of physiological properties, such as heart rate or breathing frequency. As may be derived from FIG. 3a, electrically conductive contacts 310a and 310b are located on a surface 305 of the device 300. Contacts 310a and 310b are connected to contacts on a surface of the garment to establish an electrical connection to the measuring sensors.

In some embodiments, contacts 310a and 310b are the respective counterpieces to the contacts 215a and 215b or 245a and 245b or 265a and 265b. In embodiments in which the contacts of the garment are formed as hook/loop bands of a Velcro® fastener, the contacts 310a and 310b are the respective counterpieces of the Velcro® fastener, as described above.

Furthermore, a number of interface outputs 320 can be located on a surface of the device 300, such as an USB output, a firewire output, an Ethernet output or a flash-card drive.

FIG. 3b shows a perspective view of the device 300, in which the surface 350 opposing surface 305 can be seen. In some embodiments, a display 360 is integrated into this surface 350, on which for instance current measuring values can be displayed. Furthermore, a keypad 370 is attached so that the device 300 can be operated directly via the keypad 370 for instance by the aid of the display 360.

FIG. 4 schematically shows a perspective view of the device 300 according to an exemplary embodiment. The individual modules of the device 300 can be connected to one another via a bus. The main function of the processor 425 is to process and evaluate the physical signals received by the measuring sensors via contacts 480 (corresponding to contacts 310a and 310b of FIG. 3a). The processor is coupled to a measuring electronics 470, which is adapted to detect the physical signals, such as the electrical potentials in the case of a heart rate measurement. The processor 425 then conducts the evaluation of the measuring signals of the memory 430 and/or to the transmission unit 410.

As described several times above, the transmission unit 410 can as an alternative also be accommodated in an external device. In all cases, the transmission unit 410 transmits the measuring results via radio to an external received. In some embodiments, the device 300 also has a GSM/GPRS/UMTS module 465, which is for instance integrated in the transmitter 410. In such embodiments, the measuring results can also be transmitted via a telecommunication network. If the device 300 has a wi-fi module 455, which can also be integrated into the transmission unit 410, the measuring results can also be transmitted via a WLAN to an external receiver.

The processor 425 is also adapted to deposit the measuring results in the memory 430. From there, the measuring results can be transmitted by means of USB interface 440, firewire interface 445, Bluetooth interface 450, Ethernet interface 460 or flash-card drive 435 to an external receiver. As an alternative, the measuring results can also be displayed on the display 405 by means of a command input via keypad 420.

In some embodiments, the device 300 also has a GPS receiver 415. By means of the GPS receiver 415 the position of the player during the training can be determined. The GPS coordinates can then together with the physiological properties measured be stored in the memory and/or they can be transmitted directly to an external receiver by means of the transmitter 410 and/or the modules 465 or 455. Conclusions can for instance be drawn to the running pensum during a game, and by the aid of the heart rate measurement the fitness of the athlete can be estimated. Precise statements about the speed of a player and the associated heart rate (or other measure physiological properties) can be determined.

The power supply of the device 300 can be ensured by batteries.

Thus, the present invention offers in its embodiments various possibilities for monitoring physiological properties of an athlete during exercising his/her sport, without impeding the athlete or without increasing the risk of injury. Furthermore, the risk of a damage to the measuring sensors and of the measuring electronics is reduced.

Although the invention is described with respect to the physical embodiments, which are established according to the invention, the person skilled in the art recognizes that various modifications, variations and improvements of the present invention in the light of the above teachings and within the scope of protection of the enclosed claims can be carried out without leaving the spirit and the intended scope of protection of the invention. Furthermore, those areas from which it is assumed that the person skilled in the art is familiar therewith were not described in order not to unnecessarily obscure the invention described therein. Thus, the invention is not to be considered as restrictive by the special illustrative embodiments, but only by the scope of the enclosed patent claims.

The invention claimed is:

1. An article comprising:
a garment;
a monitoring device for monitoring physiological properties of a person wearing the garment, wherein the monitoring device is positioned on a rear side of the garment, wherein the monitoring device is adapted to receive and further process physical signals characterizing the physiological properties to be monitored of the person wearing the garment, and wherein the monitoring device is adapted to store and transmit measuring results resulting from the further processing of the physical signals, the monitoring device being detachably connected to the garment and comprising conductive contacts on a surface;
two conductive electrodes;
conductive contacts on a surface of the rear side of the garment; and
conductive connections from the conductive electrodes to the conductive contacts of the monitoring device through the conductive contacts of the garment;
wherein the conductive contacts of the monitoring device can detachably be connected to the conductive contacts of the garment;
the conductive electrodes form an inner surface of the garment;
the conductive electrodes are located symmetrical with respect to a spine of the person wearing the garment when the garment is worn; and
each of the conductive electrodes extends laterally between floating ribs and a costal arch of the person wearing the garment beginning at a front side of the garment in the direction towards the rear side of the garment up to between scapulae of the person wearing the garment when the garment is worn.

2. An article as claimed in claim 1, wherein:
the conductive electrodes are made of conductive stretch fabric;
the conductive connections from the conductive electrodes to the conductive contacts of the garment are made of conductive thread; and
the conductive contacts on the surface of the rear side of the garment and the conductive contacts on the surface of the monitoring device are hook and loop fasteners.

3. An article as claimed in claim 1, wherein the garment also comprises non-conductive fibers and the conductive connections from the conductive electrodes to the conductive contacts of the garment are woven into the non-conductive fibers of the garment on the surface of the garment.

4. An article as claimed in claim 1, wherein at least part of the garment is made of non-conductive fibers, and the conductive connections from the conductive electrodes to the conductive contacts of the garment are adhered or stitched onto the surface of the garment onto the part of the garment that is made of non-conductive fibers.

5. An article as claimed in claim 1, wherein the monitoring device further comprises a processor, a memory, an USB interface, a firewire interface, a wi-fi module, a Bluetooth interface, a GSM module, a GPRS module, an UMTS module or a GPS module.

6. An article as claimed in claim 1, wherein the physiological properties to be monitored measure the heart rate of the person wearing the garment, and the monitoring device is configured to measure electrical potentials at the electrodes.

7. An article as claimed in claim 1, wherein:
the conductive contacts of the garment are attached on an outer surface on the rear side of the garment; and
the conductive contacts of the garment are located in the state worn either left or right of the spine of the person wearing the garment.

8. An article as claimed in claim 7, wherein:
the conductive contacts of the garment when being worn are located in a shoulder area of the person wearing the garment; and
the conductive connections from the conductive electrodes to the conductive contacts have an identical electrical resistance.

9. An article as claimed in claim 7, wherein:
the conductive contacts of the garment are located when being worn in a loin area of the person wearing the garment; and
the conductive connections from the conductive electrodes to the conductive contacts have an identical electrical resistance.

10. An article as claimed in claim 1, wherein:
the conductive contacts are attached on an outer surface on the rear side of the garment; and
the conductive contacts of the garment are located when being worn symmetrically right and left of the spine of the person wearing the garment.

11. An article as claimed in claim 1, wherein:
the conductive contacts are attached on an inner surface on the rear side of the garment; and
the conductive contacts of the garment are located in the neck area of the person wearing the garment when being worn.

* * * * *